United States Patent [19]

Simmonds et al.

[11] Patent Number: 5,900,375
[45] Date of Patent: May 4, 1999

[54] INDUCTION OF EMBRYOGENESIS USING CYTOSKELETON INHIBITORS OR PROTEIN SYNTHESIS INHIBITORS

[75] Inventors: Daina H. Simmonds, Nepean; William Newcombe, Battersea, both of Canada

[73] Assignees: Her Majesty the Queen in right of Canada, as represented by Agriculture; Agri-Food Canada, a part interest, both of Ottawa, Canada

[21] Appl. No.: 08/623,523

[22] Filed: Mar. 29, 1996

[51] Int. Cl.⁶ ....................................................... C12N 5/00
[52] U.S. Cl. ........................... 435/410; 435/420; 435/431; 435/242; 47/58
[58] Field of Search ................................... 435/410, 420, 435/431, 242; 47/58

[56] References Cited

PUBLICATIONS

W.A. Keller et al., Embryogenesis and Plant Regeneration in *Brassica napus* Anther Cultures. *Can. J. Bot.* (1977) 55:1383–1388.
Astrid Gland et al., Genetic and Exogenous Factors Affecting Embryogenesis in Isolated Microspore Cultures of *Brassica napus* L. *Plant Physiol,* (1988) 132:613–617.
W.A. Keller et al., High Frequency Production of Microspore–derived Plants from *Brassica napus* Anther Cultures, *Z. Pflanzenzuchtg,* (1978) 80:100–108.
G. Wenzel et al., Anther Culture as a Breeding Tool in Rape, *Z. Pflanzenzuchtg,* (1977) 78:149–155.
M.C.M. Iqbal et al., Increased Embryogenesis after Colchicine Treatment of Microspore Cultues of *Brassica napus* L., *J. Plant Physiol,* (1994) 143:222–226.
M.A.M. Zaki et al., Microspore–derived Embyros in *Brassica:* The Significance of Division Symmetry in Pollen Mitosis I to Embryogenic Development. *Sex Plant Reprod.* (1991) 4:48–55.
Z.Z. Chen et al., Efficient Production of Doubled Haploid Plants through Chromosome Doubling of Isolated Microspores in *Brassica napus. Plant Breeding,* (1994) 113:217–221.
C. Mollers et al., Efficient Production of Doubled Haploid *Brassica napus* Plants by Colchicine Treatment of Microspores. *Euphytica,* (1994) 75:95–104.
Z. Fan et al., Development of Microspores in vivo and in vitro in *Brassica napus* L. *Protoplasma.* (1988) 147:191–199.
Phan V. Chuong et al., High Frequency Embryogenesis Through Isolated Microspore Culture in *Brassica Napus* L. and *B. Carinata* Braun. *Plant Science,* (1985) 39:219–226.

Regine Mathias et al., Effective Diploidization of Microspore–Derived Haploids of Rape (*Brassica napus* L.) by In Vitro Colchicine Treatment. *Plant Breeding,* (1991) 106:82–84.
N.C. Subrahmanyam et al., Chromosome Doubling of Barley Haploids by Nitrous Oxide and Colchicine Treatments. *Can. J. Genet. Cytol.* (1975) 17:573–583.
C.–S. Loh et al., The Response of Haploid Secondary Embryoids and Secondary Embryogenic Tissues of Winter Oilseed Rape to Treatment with Colchicine. *New Phytol.,* (1983) 95:359–366.
B. Barnabas al., Direct Effect of Colchicine on the Microspore Embryogenesis to Produce Dihaploid Plants in wheat (*Triticum aestivum* L.). *Theor. Appl. Genet.,* (1991) 81:675–678.
L.G. Burk et al., Diploidized Haploids From Aseptically Cultured Anthers of *Nicotiana tabacum. The Journal of Heredity,* 355–360.
Y. Wan et al., Efficient Production of Doubled Haploid Plants Through Colchicine Treatment of Anther–Derived Maize Callus. *Theor. Appl. Genet.,* (1989) 77:889–892.

*Primary Examiner*—Leon B. Lankford, Jr.
*Attorney, Agent, or Firm*—Heslin & Rothenberg, P.C.

[57] ABSTRACT

Embryogenesis from plant microspores is routinely induced with a 16–24 h temperature treatment of 32.5° C. Continuous culture at 25° C. results in pollen development. However, microspore treatment with anti-cytoskeletal agents, or protein synthesis inhibitors, at the non-inductive temperature of 25° C., can induce embryogenesis, thus demonstrating that heat shock is not required for embryogenic induction. Furthermore, when anti-microtubule agents (e.g. colchicine) are used, embryo induction and chromosome doubling occur simultaneously, thus generating doubled haploids, whereas heat induction generates haploids. Thus, the use of microtubule inhibitors will provide a simple one-step process to simultaneously induce embryogenesis and chromosome doubling for the production of fertile plants, thus providing minimal manipulation which will be very advantageous for genetic studies and plant breeding programs. As noted, heat shock induces haploids. A low level of chromosome doubling can be obtained by adding colchicine to microspore cultures during the heat treatment. However, the use of trifluralin with the heat treatment, to generate doubled haploid plants results in an improved recovery of fertile doubled haploid plants than previously shown in the prior art.

11 Claims, 3 Drawing Sheets

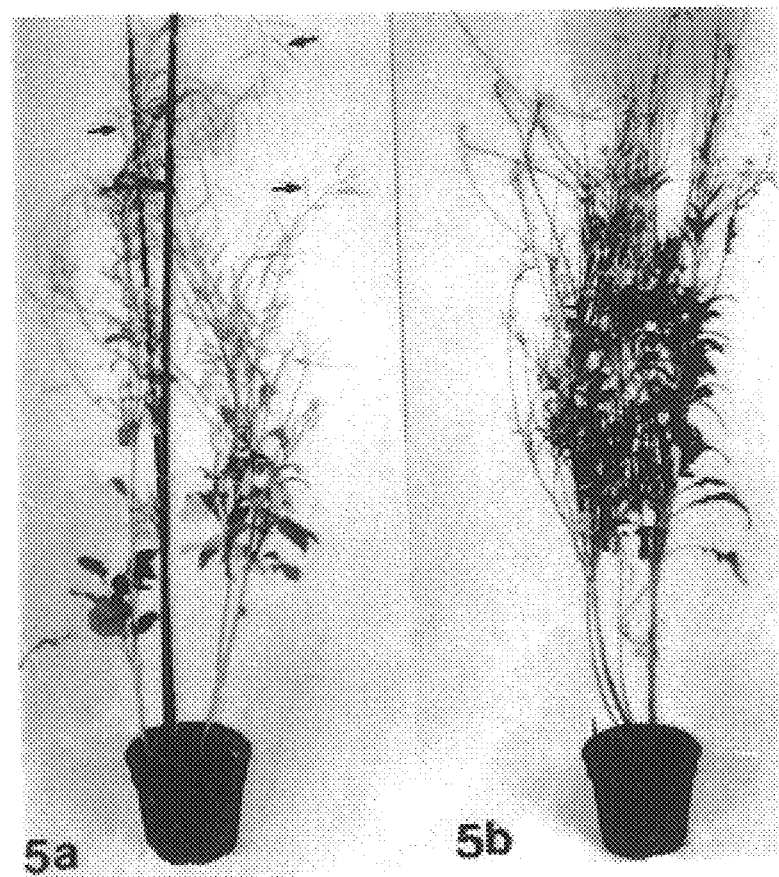
FIG.5a  FIG.5b
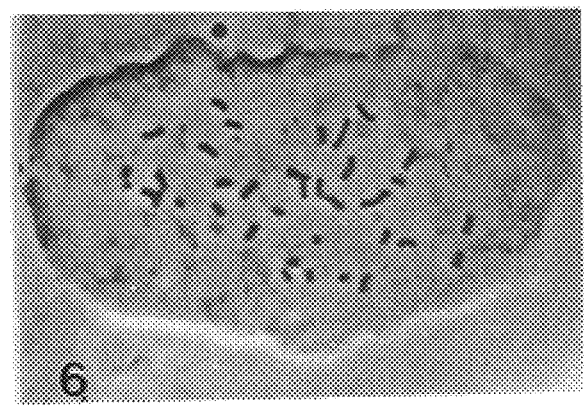
FIG.6

INDUCTION OF EMBRYOGENESIS USING CYTOSKELETON INHIBITORS OR PROTEIN SYNTHESIS INHIBITORS

FIELD OF THE INVENTION

The present invention is directed to the use of cytoskeleton modifiers or protein synthesis inhibitors to induce embryogenesis from plant microspores.

BACKGROUND AND PRIOR ART

The production of haploid plants generated through either anther or isolated microspore culture has succeeded in over 240 species from 85 genera in 38 families (Srivastava and Johri 1988). Microspore culture of *Brassica napus* has become one of the most efficient embryogenic systems and has been exploited for developmental studies (e.g. Zaki and Dickinson 1991; Telmer et al. 1992, 1993, 1994), for mutagenesis and gene transfer (Swanson et al. 1989; Huang 1992), and for development of doubled haploid homozygous breeding lines (Chen and Beversdorf 1992). The use of haploid plants, generated from anther or microspore culture, has enhanced the efficiency of crop improvement programs (Collins and Genovesi 1982, Chen and Beversdorf 1992). Although haploid plants can be readily regenerated, the haploids cannot be used directly in genetic studies and breeding programs because they are sterile (Subrahmanyam and Kasha 1975). The current methods of doubling the chromosome complement of haploids to produce fertile homozygous doubled haploids are inefficient and labor intensive.

Efficient induction of embryogenesis is necessary for developmental and biochemical studies. The efficiency of embryogenesis of *B. napus* has been improved by using donor plants grown at low temperatures (Keller et al. 1986), by optimizing the microspore culturing conditions (Keller et al. 1986; Lichter 1981; Fan et al. 1988; Chuong and Beaversdorf 1985; Kott et al. 1988; Gland et al. 1988; Huang et al. 1990) and by using microspores at the competent developmental stages (Telmer et al. 1992).

Exposure of microspores to a high temperature (32.5° C.) is considered to be a key factor for induction of embryogenesis (Keller and Armstrong 1978; Cordewener et al. 1994) and it has been proposed that heat shock proteins play a role in the inductive process (Pechan et al. 1992). Several unique proteins, synthesized during heat induction, have been identified and it has been suggested that they may be early markers of embryogenesis or heat shock proteins involved in the induction process (Cordewener et al. 1994). However, with the use of heat shock to induce embryogenesis, it is very difficult to distinguish between factors associated with the heat shock process and those specific to the embryogenic process. Attempts to replace heat induction with alternate methods such as gamma irradiation or ethanol treatments resulted in very low embryo induction (Pechan and Keller 1989). However, the induction of sporophytic development, by means other than heat, would be very valuable to allow discrimination of heat shock factors and embryogenic factors and thereby identify the critical events involved in the change from gametophytic to sporophytic development.

Microspore morphology is altered by the 32.5° C. heat treatment. Although several morphological changes have been identified in *B. napus* cv. Topas, including the appearance of cytoplasmic granules and organelle-free regions, plasma membrane associated electron-dense deposits, and microtubule reorganization, the most prominent change is the dislocation of the nucleus (Fan et al. 1988; Simmonds et al. 1991; Telmer et al. 1993, 1994; Simmonds 1994). During pollen ontogenesis the nucleus of an early and mid-unicellular (MU) microspore is centrally located; during vacuolar enlargement, it is relocated to a lateral position, the unicellular-vacuolate stage (UV); and it remains appressed to the edge of the cell in the late-unicellular (LU) stage after the disappearance of the large vacuole (Telmer et al. 1992, 1993). The LU microspore enters the first pollen mitosis which is acentric and results in an asymmetrical division comprising a small generative cell and a large vegetative cell separated by an unstable cell wall (Telmer et al. 1993). If the LU microspore is subjected to the heat treatment, the nucleus migrates to a more central position where mitosis occurs and ultimately results in a symmetrical division with two daughter cells similar in size and organelle distribution, and separated by a stable cell wall (Fan et al. 1988; Telmer et al 1993; Simmonds 1994); the symmetric division blocks further pollen development and identifies the induced structures (Telmer et al. 1994). An early structural marker which predicts a change in microspore division symmetry is a preprophase band (PPB) of microtubules; the PPB, a cortical ring of microtubules, appears in the medial region of the microspore after only about 6–8 h of heat treatment (Simmonds et al. 1991; Simmonds 1994). PPBs have not been observed during pollen development (Van Lammeren et al. 1985; Terasaka and Niitsu 1990; Simmonds et al. 1991). As the PPBs predict the position of the future division plane in organized (Gunning and Hardham 1982) and disorganized tissue (Simmonds 1986), and may have a role in wall stabilization (Mineyuki and Gunning 1990), it has been proposed that microtubule reorganization is a key event in changing developmental patterns where altered division symmetry and cell wall dynamics define the induced embryogenic structure (Simmonds 1994).

Spontaneous diploids have been reported to arise from anther culture of barley (Subrahmanyam and Kasha 1975), tobacco (Burk et al. 1972, Kasperbauer and Collins 1972;), corm (Ku et al. 1981) and *B. napus* (Charne et al. 1988). It has been hypothesized that diploids may occur through endomitosis, endoreduplication and/or nuclear fusion within the cell during early stages of culture (Sunderland et al. 1974, Keller and Armstrong 1978) and possibly from unreduced gametes (Wenzel et al. 1977, Chen and Beversdorf 1992). However, as the occurrence of spontaneous diploids is an infrequent and inconsistent event, colchicine has been used to increase the frequency. The techniques of colchicine application has not changed much since Levan (1938) soaked onion roots in colchicine solutions. Currently, apical meristems, secondary buds, tillers or roots are treated with colchicine (see Wong 1989, Swanson 1990, Mathias and Robbelen 1991). Generally, about 50% of the treated plants are responsive. These procedures are labor intensive (Chen and Beversdorf 1992), hazardous (Depaepe et al. 1981, Hansen et al. 1988, Barnabas et al. 1991, Hassawi and Liang 1991) and costly (Hassawi and Liang 1991) because high concentrations of colchicine are needed. Furthermore, three months can be added to the plant regeneration time to recover homozygous lines (Beversdorf et al. 1987). Additional drawbacks to using this approach include the regeneration of chimeras (Hansen et al. 1988, Wan et al. 1989, Wong 1989, Swanson 1990, Bamabas et al. 1991), aneuploids (Zhao and Davidson 1984), abnormalities in plant development (Hart and Sabnis 1976, Loh and Ingram 1983) and low seed yield. Application of colchicine to cultures prior to organ formation has produced non-chimeric doubled haploids from corn callus (Wan et al. 1989) and wheat anther culture (Barnabas et al. 1991). An effective alternative to colchicine has not been reported to date but would be highly desirable (Wan et al. 1989, Hassawi and Liang 1991).

Trifluralin, a dinitroaniline herbicide (Probst et al. 1976), acts in a manner similar to colchicine, by disrupting spindle microtubules (Bartels and Hilton 1973). Trifluralin, unlike colchicine, has a higher affinity for plant tubulin than for animal tubulin (Hess and Bayer 1977, Morejohn and Fosket 1984, Morejohn et al. 1984).

Non-chimeric doubled haploid plants were recovered from B. napus cv. Topas microspores cultured in the presence of colchicine or trifluralin, according to the present invention. These antimitotic agents were applied during the initial stages of culturing, while the microspores were undergoing the heat treatment (32.5° C.) used to induce embryogenesis. Trifluralin treated cultures generated normal embryos which germinated directly upon transfer to regeneration medium and produced doubled haploid plants at frequencies approaching 60%. However, only about 20% of the plants recovered from colchicine treated cultures were doubled haploids. Longer colchicine treatments resulted in higher frequencies of fertile plants but embryo development was abnormal and several subcultures were required to induce plant development. Chen et al. (1994) also found that the cv. Topas responded negatively to colchicine treatment, however other cultivars responded positively by increasing the production of embryos and the frequency of fertile plants. However, it has been shown that colchicine can be used, instead of heat, to induce embryogenesis from B. napus cv. Topas microspores. The embryos generated from colchicine-induced cultures, at non-inductive temperatures were normal. Ninety percent of the plants recovered from these embryos were fertile.

Desirable genetic recombinants resulting from microsporogenesis can be exploited by recovering haploid plants from microspore derived embryos. The interesting recombinants can be used for the development of new varieties or homozygous breeding lines. As haploid plants are sterile, the practical utilization of haploids in breeding programs relies on an efficient chromosome doubling technique to obtain fertile diploid plants (Subrahmanyam and Kasha 1975, Loh and Ingram 1983).

SUMMARY OF THE INVENTION

The purpose of this present invention was to demonstrate that microspore treatment with anti-cytoskeleton agents or inhibitors of protein synthesis, at a non-inductive temperature, is sufficient to induce embryogenesis from plant microspores. This present invention shows that colchicine, a microtubule depolymerizing agent can induce microspores to undergo embryogenesis and that heat shock is not required. The present invention further shows that 90% of the plants regenerated from the colchicine-induced embryos were doubled haploids.

The standard prior art methods of inducing embryogenesis rely on exposing the microspores to a high temperature, usually about 32.5° C. This method has been used to induce embryogenesis in a number of plant species, as fully discussed in the prior art. Haploid plants can readily be regenerated from the embryogenic microspore cultures. However, these haploid plants are sterile and, therefore, not useful in genetic studies and breeding programs. As discussed above, colchicine has been used with some success to double the chromosome compliment in the cell and thus results in doubled haploids.

The present invention is further directed to the use of trifluralin, a dinitroaniline herbicide which acts in a manner similar to colchicine by disrupting spindle microtubules. However, as described herewith, the application of colchicine or trifluralin during heat induction resulted in the recovery of a much higher frequency of doubled haploid plants from the trifluralin treatment.

Thus, according to the present invention, there is provided a method of inducing embryogenesis from plant microspores comprising:
 treating a microspore plant culture with a sufficient amount of a cytoskeleton inhibitor or a protein synthesis inhibitor at non-heat shock temperature; and
 incubating for a sufficient time to induce embryogenesis.

According to the present invention there is provided a further method of inducing embryogenesis and chromosome doubling from plant microspores comprising:
 treating a microspore plant culture of B. napus cv. Topas with 25 $\mu$M of colchicine at 25° C.;
 incubating the microspore plant culture for 42 hours to induce embryogenesis and chromosome doubling;
 reducing the colchicine to 12.5 $\mu$M by dilution; and
 incubating at 25° C. for 3 to 4 weeks until embryos are formed.

Further, according to the present invention, there is provided a method of producing doubled haploid plants from plant microspores comprising:
 treating a microspore plant culture with a sufficient amount of a microtubule inhibitor at a heat shock temperature for a sufficient time to induce chromosome doubling.

In addition according to the present invention there is provided a method of producing doubled haploid plants from plant microspores comprising:
 treating a microspore plant culture of B. napus with from 1 $\mu$M to 10 $\mu$M trifluralin for 18 hours at 32.5° C. to induce chromosome doubling;
 removing the trifluralin from the microspore culture and incubating at 25° C. for 3 to 4 weeks until embryos are formed.

BRIEF DESCRIPTION OF THE DRAWINGS

FIGS. 5a and 5b show mature plants from colchicine-induced microspore cultures (FIG. 5a) (fertile plants, pods shown at the arrows) and heat-induced microspore cultures (FIG. 5b).

FIG. 6 is a root tip cell showing the chromosome number of 2n=38. The Feulgen stain was used on root tips of progeny from a plant regenerated from microspore-derived embryos induced by colchicine treatment.

DETAILED DESCRIPTION OF THE INVENTION

Figures 1A, 1B:
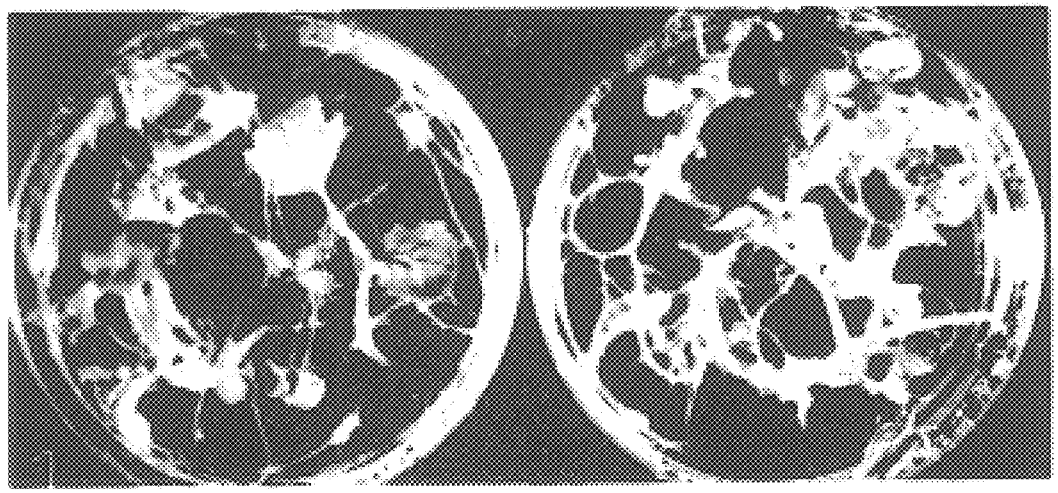
FIGS. 1a and 1b show germinated embryos from colchicine-induced microspore cultures (FIG. 1a) and heat-induced microspore cultures (FIG. 1b).

The purpose of this invention was to demonstrate that it is possible to induce microspores to undergo embryogenesis with agents other than a high temperature treatment. In some cases the agent will also promote doubling of the chromosome complement and thus generate doubled haploid plants.

The microspore cytoskeleton was modified with anti-microtubule or anti-microfilament agents at a non-heat shock temperature of about 25° C. Embryogenesis was induced by 18–50 hour treatments with anti-microtubule agents, namely, colchicine (10–100 uM), trifluralin (0.5–10 uM) or amiprophosmethyl (0.3–30 uM). Embryogenesis was also induced by 5–60 min. treatments with the anti-microfilament agent, cytochalasin D (10–80 uM).

Microspore protein synthesis was inhibited with cycloheximide. Embryogenesis was induced by 7–24 h treatments with cycloheximide (0.03–3.5 uM) at the non-heat shock temperature of about 25° C.

Colchicine disrupts pollen development by depolymerizing microspore microtubules and may therefore be effective in inducing embryogenesis in a variety of species, including the more recalcitrant ones.

According to the present invention, microspores are incubated with from 12.5 $\mu$M to 100 $\mu$M colchicine at non-heat shock temperatures, for example, at about 25° C. for about 15 to about 50 hours. Following this initial treatment, the concentration of the colchicine is reduced and the treated microspore cultures are further incubated at approximately 25° C. until embryos form.

After the initial treatment of the microspore cultures with colchicine, the concentration of the colchicine is reduced. In one example of the present invention, the colchicine concentration is diluted by adding approximately an equal volume of fresh medium which does not contain any colchicine. In a further example of the present invention, the colchicine is removed by washing the treated microspores and resuspending the washed microspores in fresh culture medium.

In one example of the present invention, the microspore culture is treated with 25 $\mu$M to 50 $\mu$M colchicine for 18 to 48 h at 25° C. In a further example of the present invention, the microspores are cultured with 25 $\mu$M colchicine at 25° C. for 42 h, followed by medium dilution.

Improved results were obtained when the microspore culture preparations were staged for early development. It was found that either the unicellular-vacuolate (UV) stage or the late-unicellular (LV) stage resulted in the highest percentage of embryo generation. In these two stages, more than 78% of the microspores are unicellular microspores. This is in contrast to the known results for heat-treated microspores wherein the higher frequency of embryo production is obtained from mature microspores (less than 75% unicellular).

The present invention is further directed to the use of colchicine or trifluralin to generate doubled haploid plants, where heat treatment is used to induce embryogenesis. In this example of the invention, cultured microspores are incubated from approximately 30 to 35° C. in either colchicine at 12.5 to 25 $\mu$M or trifluralin at 1 to 10 $\mu$M for 0.5 to 18 h. After this initial incubation period, the microspores are washed to remove the colchicine or trifluralin. The cultures are then incubated at 25° C. from about 3 to 4 weeks until cotyledonary embryo development.

According to this aspect of the invention, it was found that the addition of low concentrations of trifluralin (1 to 10 $\mu$M) to embryogenic microspore cultures provides a simple approach to doubling chromosome numbers to generate fertile double haploid plants. The use of trifluralin is preferred to the use of colchicine. Chimeric plants are avoided because the chromosomes are doubled very early in culture. The method is simple, effective and inexpensive. Furthermore, trifluralin is safer to use than colchicine.

In an example of the present invention, cultured microspores are incubated at 32.5° C. in 1 $\mu$M to 10 $\mu$M trifluralin for 18 h. The microspores are then washed and incubation is continued at 25° C. until embryos develop.

While this invention is described in detail with particular reference to preferred embodiments thereof, said embodiments are offered to illustrate but not limit the invention.

EXAMPLES

Example 1

Induction of Embryogenesis with Colchicine
Donor plants and microspore cultures

The growth conditions for donor plants of *Brassica napus* cv. Topas line 4079, and procedures for microspore developmental staging, isolation and culture were previously described (Telmer et al. 1992). For each experiment, buds were carefully selected for petal lengths ranging from 2.4–2.7 and 2.7–3.1 mm to obtain microspore populations of class II (majority of cells at the UV stage) and class III [majority of cells at the LU, and/or mitotic (M) and bicellular (BC) stages], respectively (Telmer et al. 1992).
Colchicine treatment Colchicine (Sigma Chemical Co.) stock solutions of 5 mM in water were stored at 4° C. in darkness. When required, colchicine was diluted to 50 and 100 $\mu$M in NLN-13 culture medium and filter sterilized (0.22 $\mu$m Millex-GS Millipore). Microspores were plated at a cell density of 40,000 mL$^{-1}$ in 300 $\mu$L NLN-13 in Petri dishes (30×10 mm, Falcon 1008). An equal volume of NLN-13 with 0, 50 or 100 $\mu$M colchicine was added. For each treatment at least 3 replicates were used and the dishes were placed in a plastic container at 100% humidity in an incubator at 25° C. for either 18 or 42 h in darkness.
Colchicine removal or dilution after 18 or 42 h of treatment Coichicine was either diluted by adding an equal volume of fresh NLN-13, 18 or 42 h after treatment or alternatively removed by washing. Two different washing procedures were used: i. centrifugation/pelleting and ii. collection with Spin-X tubes. In the centrifugation/pelleting procedure two volumes of washing medium [B5 (Gamborg et al. 1968) containing 0.35M mannitol] was added to the microspore cultures, transferred to sterile Eppendorf tubes and spun at 65 g for 3 min. The pellets were resuspended in washing medium and the procedure was repeated two more times and then the pellets were resuspended in fresh NLN- 13 medium and returned to culture dishes. To collect microspores with Spin-X tubes (2 mL, Microcentrifuge Filter Units, Durapore PVDF, membrane pore size 0.45 $\mu$m, Millipore), the cultures were transferred to the Spin-X tube inserts and the medium was spun through at 40 g for 2 min, while the cells remained on the surface of the Millipore membrane. Fresh NLN-13 medium was added to the surface to resuspend the cells and this was also spun through. This procedure was repeated two more times and the cells were resuspended in NLN-13 and cultured as previously described. Embryos were counted after 3–4 weeks of culture.
Controls Each experiment included plated microspores cultured continuously at 25° C., and for 18 h (Table 1) or 24 h (Table 2 and 3) at 32.5° C. followed by 25° C. Controls were also washed or diluted to mimic colchicine treatments. The frequency of embryogenesis did not differ significantly in 18 and 24 h heat treatments (data not shown).

Induction of embryogenesis with colchicine: Concentration and duration of treatment Microspores were treated with 25 or 50 μM colchicine for 18 or 42 h at 25° C. The longer colchicine treatments (42 h) resulted in higher embryogenic frequencies at both concentrations of colchicine (Table 1). Although 50 μM colchicine was usually more effective than 25 μM in treatments in which washing (centrifugation/pelleting) was used to remove colchicine, the highest embryo frequency was obtained with a 25 μM colchicine treatment of 42 h followed by medium dilution (Table 1). The lower concentration of 12.5 μM colchicine, induced embryogenesis at a much lower frequency (approx. 1.5%, data not shown).

TABLE 1

The effects of colchicine concentration, duration of treatment, and washing or dilution on embryogenesis frequencies from microspores of B. napus cv. Topas as compared to embryogenesis from heat-treated (32.5° C.) microspores.[a]

| Experiment | Duration of treatment (h) | Heat-treated % total microspores[c] | Embryo frequency | | | | |
|---|---|---|---|---|---|---|---|
| | | | | C[b]H | | | |
| | | | 0 μM[d] | 25 μM[d] | | 50 μM[d] | |
| | | | | W[e] | D[e] | W | D |
| A | 18 | 26.0 (24.0–27.3) | 0 | 0.12 | NA[f] | 0.22 | NA |
| | 42 | | | 0.35 | NA | 0.36 | NA |
| B | 18 | 13.4 (13.0–13.7) | 0 | 0.43 | 0.58 | 0.59 | 0.51 |
| | 42 | | | 0.44 | 0.88 | 0.63 | 0.56 |

[a]The results from two experiments are shown as means of at least three replicates; other experiments show the same trends.
[b]Ratio of embryo frequency of colchicine-treated (washed or diluted cultures) to heat-treated controls (cultures not washed or diluted).
[c]Embryo frequency expressed as percent of total viable microspores cultured. Figures show the average number of embryos of three replicates; range is shown in brackets.
[d]Colchicine concentration.
[e]Microspores were either washed by centrifugation/pelleting (W) or diluted (D) with an equal volume of fresh culture medium.
[f]NA—data not available.

Effects of washing or dilution of microspores on embryogenesis

Following colchicine treatment, the cells were either washed to remove the chemical or diluted to reduce its concentration. The washing procedure using centrifugation/pelleting appeared to be detrimental to efficient embryo production. Cultures which were washed after a heat treatment had a significantly lower frequency of embryogenesis (8.7%) than heat-treated cultures, which were not washed (14.4%)(Table 2). Washing by collecting microspores on membranes of Spin-X tubes was more effective than the centrifugation/pelleting method but it was costly and labor intensive (Table 2). However, the addition of an equal volume of fresh culture medium to microspore cultures, following induction, resulted in the highest embryogenic frequencies and improved embryo quality (see below). Likewise, medium dilution following colchicine treatment (25 μM) resulted in higher frequencies of embryogenesis than washing (Table 1).

TABLE 2

Effect of washing or dilution of heat-induced (32.5° C.) microspores of B. napus cv. Topas on embryogenesis frequencies.

| | | Mean embryo frequency (%) | |
|---|---|---|---|
| Treatment | No. of Experiments | Control | Treated |
| Washing: centrifugation/pelleting | 17[a] | 14.4(±0.7)[b] | 8.7(±0.8)* |
| Washing: Spin-X-tubes | 5 | 13.1(±2.0) | 11.4(±1.6) |
| Dilution[c] | 13 | 15.0(±1.1) | 15.4(±0.9) |

[a]At least three replicates were used for each experiment.
[b]The figures show the mean value of the experiments; standard errors are shown in brackets.
*Significantly different from control, P < 0.01 (F-test).
[c]The Petri dish contents were diluted with an equal volume of fresh culture medium.

Microspore developmental stage responsive to colchicine

The range in frequency of microspore embryogenesis was examined using the optimized colchicine induction conditions of 25 μM for 42 h followed by medium dilution. The sixteen experiments conducted showed that the frequency of embryo yield ranged from 0.1 to 15.2% (Table 3). Although the induction frequency appears to be inconsistent, further analysis shows that microspore responsiveness to colchicine was developmental stage specific. The data in Table 3 show that the microspore preparations which were staged for early development, (predominantly UV and LU stages or more than 78% unicellular microspores, Experiments 8–16), generated embryos at a mean frequency of 10.2% whereas only 1.6% embryos were generated from preparations staged for later development, (predominantly LU, M and BC stages or less than 75% unicellular, Experiments 1–7). Conversely, heat treatment produced a higher frequency of embryogenesis (mean of 16.1%) from the more mature microspore preparations than from the early developmental stages (mean of 8.8%). The ratios of C/H (colchicine induced/heat induced embryogenesis) also show that the two induction methods affect different microspore developmental stages.

TABLE 3

Frequencies of embryogenesis following heat (32.5° C.) or colchicine (25 μM, 42 h, 25° C.) induction of B. napus cv. Topas microspores cultured at various initial developmental stages.

| | Initial Microspore Isolation % microspores at different developmental stages[a] | | | | | | Embryogenesis % Total Microspores[c] | | |
|---|---|---|---|---|---|---|---|---|---|
| Exp. no. | MU | UV | LU | M | BC | % UC[b] | Heat-treated | Colchicine-treated | C[d]/H |
| 1 | 0 | 0 | 2 | 0 | 98 | 2 | 18.2 | 0.4 | 0.02 |
| 2 | 0 | 11 | 27 | 18 | 44 | 38 | 11.4 | 1.6 | 0.14 |
| 3 | 0 | 12 | 30 | 18 | 40 | 42 | 14.9 | 1.0 | 0.07 |
| 4 | 0 | 18 | 26 | 10 | 46 | 44 | 12.4 | 0.1 | 0.01 |
| 5 | 0 | 14 | 41 | 12 | 33 | 55 | 21.6 | 2.4 | 0.11 |

TABLE 3-continued

Frequencies of embryogenesis following heat (32.5° C.) or colchicine (25 μM, 42 h, 25° C.) induction of B. napus cv. Topas microspores cultured at various initial developmental stages.

| Exp. no. | Initial Microspore Isolation % microspores at different developmental stages[a] | | | | | | Embryogenesis % Total Microspores[c] | | C[d]/H |
|---|---|---|---|---|---|---|---|---|---|
| | MU | UV | LU | M | BC | % UC[b] | Heat-treated | Colchicine-treated | |
| 6 | 0 | 14 | 42 | 24 | 20 | 56 | 21.0 | 0.6 | 0.03 |
| 7 | 0 | 20 | 54 | 6 | 20 | 74 | 13.2 | 4.8 | 0.36 |
| | | | | | | | X̄ = 16.1(1.6)[e] | X̄ = 1.6(0.6) | |
| 8 | 8 | 18 | 53 | 15 | 6 | 79 | 13.4 | 11.8 | 0.88 |
| 9 | 2 | 31 | 49 | 12 | 6 | 82 | 9.0 | 8.3 | 0.92 |
| 10 | 10 | 54 | 24 | 0 | 12 | 88 | 14.0 | 13.6 | 0.97 |
| 11 | 8 | 49 | 40 | 1 | 2 | 97 | 7.6 | 6.1 | 0.80 |
| 12 | 20 | 50 | 27 | 2 | 1 | 97 | 7.6 | 8.5 | 1.12 |
| 13 | 8 | 53 | 37 | 2 | 0 | 98 | 9.0 | 11.0 | 1.22 |
| 14 | 5 | 66 | 29 | 0 | 0 | 100 | 9.5 | 15.2 | 1.60 |
| 15 | 25 | 64 | 11 | 0 | 0 | 100 | 6.1 | 11.7 | 1.92 |
| 16 | 34 | 36 | 29 | 0 | 0 | 100 | 3.1 | 6.1 | 1.97 |
| | | | | | | | X̄ = 8.8(1.1) | X̄ = 10.2(1.1) | |

[a]MU, mid-unicellular;
UV, unicellular vacuolate;
LU, late unicellular;
M, mitotic;
BC, bicellular.
[b]unicellular microspores, UC = MU + UV + LU.
[c]Embryo frequency of heat-treated or colchicine-treated cultures expressed as percent of total viable microspores cultured.
Colchicine treatments were diluted after 42 h of culture. Each figure represents the mean embryo frequency of at least three samples.
[d]Ratio of embryo frequency of colchicine-treated (C) microspores to heat-treated (H) microspores.
[e]S.E. is shown in brackets.

Quality of colchicine-induced embryos

The quality and yield of embryos in cultures induced with 25 μM colchicine and diluted after 42 h of treatment was superior to cultures washed after treatment or treated continuously with 25 μM colchicine but comparable to the heat-induced cultures which were diluted after 42 h of culturing. It is noteworthy that the embryo quality of the heat-induced cultures was improved by dilution with fresh culture medium. The rate of development of colchicine-induced microspores was initially slower by 3–4 days than that of the heat-induced microspores. However, there was no obvious difference in the size of embryos induced by these two different treatments after 4 weeks of culture. A swelling of the hypocotyl region in some embryos induced by colchicine was observed, but this did not affect embryo germination. The embryos generated from 50 μM colchicine treatments followed by medium dilution formed large globular structures and developed abnormally.

The significant finding in this invention is that colchicine can induce embryogenesis from microspores of B. napus cv. Topas at the non-inductive temperature of 25° C. Therefore a heat shock is not required to induce embryogenesis. Colchicine-induced microtubule depolymerization can change microspore development from gametogenesis to embryogenesis provided that the microspore isolate is predominantly UV and LU, or more specifically, more than 78% unicellular. Colchicine specificity for the unicellular microspore is most probably a result of microtubule susceptibility to colchicine at the unicellular stage; another study reported that colchicine treatment resulted in complete depolymerization of unicellular microtubules whereas the microtubules of bicellular microspores were almost unaffected.

Heat induction is optimal in microspore isolates containing more advanced developmental stages, namely LU, M and BC (less than 75% unicellular) or Class III (Telmer et al. 1992). The two inducing agents, heat and colchicine, appear to act on different microspore developmental stages, however this is partly due to the fact that they require different periods of time to exert their effects. Nuclear migration away from the edge of the cell and the appearance of PPBs after about 6 h of heat treatment indicate that morphological changes including microtubule reorganization occur very rapidly with heat induction (Simmonds 1994; Telmer et al. 1995). Colchicine induction requires a longer period of time. Cell growth and development is slower at 25° C. than at 32.5° C. Microtubule depolymerization by colchicine is a slow process, requiring up to 8 h. Following microtubule depolymerization, the nucleus migrates away from the edge of the cell. This indicates that microtubules have a role in nuclear anchoring and maintaining cell asymmetry in pollen development (Simmonds 1994). During the time period needed for microtubule depolymerization, microspore development continues and some of the microspores which began as UV or LU, at culture initiation, arrive at mitosis with depolymerized microtubules and a centrally located nucleus, primed to undergo a symmetrical division. Therefore, the LU microspore which enters mitosis with altered morphology remains the competent or inducible stage for both inducing agents. However, the LU microspores which enter mitosis during the initial phase of culturing escape the effects of colchicine and divide asymmetrically, as pollen; as these bicellular microspores are insensitive to colchicine, they continue normal pollen development in its presence. However, it has been shown that a high frequency of maturing bicellular microspores inhibit the development of induced microspores, possibly by releasing some inhibitory factor(s) (Kott et al. 1988; Simmonds et al. 1991). Therefore, the requirement of predominantly unicellular microspores for colchicine induction may be due to a combination of factors, including microspore susceptibility to colchicine at the unicellular stage, slow microtubule depolymerization, relatively slow cell development at 25° C. and embryogenic inhibitory properties of maturing bicellular microspores.

As colchicine induction and heat induction target different initial microspore populations, it seems reasonable to expect that the combination of the two treatments would result in a greater yield of embryos than the individual treatments. However, simultaneous heat and colchicine treatments was reported to reduce embryogenesis in B. napus cv. Topas (Chen et al. 1994). Contrary to these results, an increase in embryogenesis was reported by Zaki and Dickinson (1991) and Iqbal et al. (1994). As these workers did not stage their microspore populations, this combination of treatments may be beneficial when heterogeneous populations of microspores are cultured or when embryogenesis is low. It may not enhance embryogenesis when microspore isolations are screened for optimal developmental stages and very high embryogenic frequency has been attained with heat induction alone.

The appearance of PPBs and the change in microtubule organization during heat induction may be the result of heat shock. All organisms that have been examined to date respond to heat shock by synthesizing heat shock proteins and simultaneously inhibiting the synthesis of housekeeping proteins (Vierling 1991). While heat shock proteins have been proposed to be involved in the induction of B. napus cv. Topas microspore embryogenesis (Pechan et al. 1991; Cordewener et al. 1994) it is possible that the inhibition of synthesis of certain pollen-specific proteins which may be concomitant with heat shock could be more important. Such proteins may participate in maintaining morphological asymmetry and their removal would lead to a loss in cell asymmetry as indicated by microtubule reorganization and nuclear migration. Once this asymmetry is lost it may not be possible to re-establish it. Thus embryogenesis may occur as a default mechanism as previously suggested (Telmer et al. 1992, 1994; Simmonds 1994). Colchicine binds to α and β tubulin heterodimers which inhibits further dimer addition to microtubules and results in eventual microtubule depolymerization (Hart and Sabins 1976; Margolis and Wilson 1977; Sternlicht et al. 1983). The elevated concentration of free tubulins acts to depress the synthesis of new α and β tubulins (Cleveland et al. 1983; Lau et al. 1985). The increase in concentration of free tubulins may also depress the synthesis of pollen specific tubulins (Carpenter et al. 1992) and thus prevent the progression of pollen development. However, the primary action of colchicine, microtubule depolymerization, releases the anchored nucleus thus disrupting microspore asymmetry (Simmonds 1994). Although heat induction and colchicine induction of microspores may act optimally at different points in microspore development they both appear to function through a default mechanism, by reorganizing the cytoskeleton, which leads to a loss of cell asymmetry and blocks pollen development.

Thus, colchicine can be used to induce microspore embryogenesis in B. napus cv. Topas. Colchicine disrupts pollen development by depolymerizing microspore microtubules and may therefore be effective in inducing embryogenesis in a variety of species including the more recalcitrant ones. Colchicine induction of embryogenesis adds another dimension in the study of induction processes; by comparing colchicine- and heat-induced embryogenesis it will be possible to distinguish factors specific to embryogenesis and those specific to heat-induction. Another advantage in using colchicine is that it is also a chromosome doubling agent and over 90% of the plants regenerated from the colchicine-induced embryos were found to be doubled haploids. A simple one step process to simultaneously induce embryogenesis and chromosome doubling for the production of fertile plants is very advantageous for genetic studies and plant breeding programs.

Microspore Embryogenesis

Plant growth conditions for B. napus cv. Topas, line 4079 and the procedures for microspore isolation, culture and induction of embryogenesis with a heat treatment (32.5°, 24 h) was previously described (Telmer et al. 1992). Microspore embryogenesis was induced at the non-inductive temperature of 25° C. by treating microspore cultures with 25 μM colchicine for 42 h followed by dilution to 12.5 μM with fresh culture medium as described above.

Plant regeneration

Cotyledonary embryos derived from both heat (32.5° C.) and colchicine (25° C.) treated microspores were subcultured onto solid B5 medium (Gamborg et al. 1968) containing 2% sucrose and 0.2% gelrite (Kelco, Division of Merck and Co. Inc., San Diego, Calif.), and cultured at 20° C. at a 16 h photoperiod [illumination provided by incandescent and fluorescent lights (90 $\mu$mol$^{-2}$s$^{-1}$)]. Plantlets at the 3 leaf stage were transferred to soil (3 cm pots) and were maintained in a mist chamber for 2 weeks. They were then repotted in 15 cm pots and grown to maturity in the greenhouse at 20/15° C. day/night at a photoperiod of 16 h and light intensity of 280 $\mu$mol$^{-2}$s$^{-1}$.

Determination of fertility

Evaluation of fertility for all regenerated plants was based on bud and flower size, pollen production and seed set. Plants producing pollen were bagged for self pollination Cytological analysis Chromosome numbers of the progeny of fertile plants was determined as previously described.

Plantlet regeneration and development

Figures 2A, 2B:
FIGS. 2a and 2b show young plants from colchicine-induced microspore cultures (FIG. 2a) and heat-induced microspore cultures (FIG. 2b).
Figures 3A, 3B:
FIG. 3a and 3b show flowering plants from colchicine-induced microspore cultures (FIG. 3a) (fertile plants) and heat-induced microspore cultures (FIG. 3b).
Figures 4A, 4B:
FIGS. 4a and 4b show influoresences from colchicine-induced microspore cultures (FIG. 4a) (fertile plants) and heat-induced microspore cultures (FIG. 4b).

Cotyledonary embryos derived from heat- and colchicine-treated microspores were subcultured onto solid regeneration medium. The embryos germinated and developed to the three leaf stage within three weeks in 32 of 80 and 59 of 120 heat-induced and colchicine-induced embryos, respectively (FIG. 1, Table 4). Plants were regenerated from these plantlets (FIG. 2). Lateral branching and leaf sizes were similar in all the regenerated plants (FIG. 3). However, 90% of the colchicine-derived plants produced much larger buds and flowers than the heat-derived plants (FIG. 4.). These colchicine-derived plants produced pollen, were fertile and had normal seed set (FIG. 5, Table 4); 94% of the heat-derived plants had vestigial anthers, no pollen and were sterile (FIG. 6, Table 4). Neither group produced any sectored plants.

TABLE 4

Plant regeneration, fertility and ploidy levels from heat induced and colchicine induced embryos of *Brassica napus* cv. Topas.

| Mode of induction of embryogenesis | Embryos cultured | Plants regenerated | Fertile Plants | Ploidy level |
|---|---|---|---|---|
| Colchicine (25° C.) | 120 | 59 | 53 | 2n = 38[a] |
| Heat (32.5° C.) | 80 | 32 | 2 | 2n = 38 |

[a]Ploidy levels were determined from germinated seeds of 30 randomly selected plants, and 2 fertile plants from the colchicine and heat induced embryogenesis, respectively. They all showed 2n = 38 chromosomes.

Cytological analysis

The ploidy levels of the progeny of fertile plants derived from both heat- and colchicine-induced embryos was examined cytologically. Seeds were germinated from the 2 plants derived from heat induction and 30 randomly selected plants derived from coichicine induction. All of the progeny showed 2n=38 chromosomes (FIG. 6).

Thus, the microtubule depolymerizing agent, colchicine, used to induce embryogenesis in microspores can simultaneously double the ploidy level of the haploid cells. Sectored chimeras were not produced. The procedure is very simple, normal embryos are generated and fertile plants are regenerated rapidly. There are many advantages implicit in this procedure. Field trials and seed analysis can begin immediately because seed yield is high. The elimination of an additional growth cycle reduces cost and speeds up variety development. It is not necessary to maintain as many plants to find doubled haploids as most will be fertile. The use of coichicine at low concentration and low volume, reduces cost and toxicity problems.

Ninety percent of plants recovered from the colchicine induced cultures, compared with 6% for heat treated cultures, developed large buds and flowers, produced abundant pollen, and set seed. The remaining plants (10% from the colchicine treatments and 94% from the heat treatments) had small buds and flowers, no pollen and did not set seed. This confirms studies (e.g. Keller and Armstrong 1978) which suggested that both bud and flower size can be used to discriminate between haploid and diploid plants. Cytological analysis of the progeny showed stable ploidy levels of 2n=38.

In addition to the genome doubling efficiency described, no chimeras or sectored plants were produced with the colchicine induction method. The fundamental difference between this method and others for production of doubled haploid plants is that unicellular microspores (Zhao et al. 1995), rather than multicellular organs were used as the target of the colchicine treatment. Chromosome doubling in the colchicine-treated cultures most likely occurred during the first microspore mitosis at which time spindles would not have formed in the presence of colchicine thus disabling chromosome segregation. Nevertheless, it is known that nuclear restitution follows, irrespective of the chromosome arrangement (e.g. Zhao and Davidson 1984). The next mitotic cycle most probably occurred after colchicine dilution, but with 2n chromosomes. Very early doubling of chromosomes could account for the absence of chimeras amongst the fertile doubled haploid plants recovered.

Approximately 50% of embryos derived from colchicine-induced microspores developed directly into normal plants. Abnormal embryo development following colchicine treatment has been observed in *B. napus, B. napus* ssp. *oleifera* (Loh and Ingram 1983) and in *Triticum aestivum* (Hansen et al. 1988). However, in the results described above, abnormal embryos were derived from microspores treated with heat to induce embryogenesis and cultured with colchicine to promote chromosome doubling; high levels of colchicine or the continuous presence of low levels undoubtedly affect embryo development (Zhao and Simmonds 1994). According to the results of the present invention, normal embryo development was seen following colchicine induction without the heat treatment. Induction of embryogenesis with colchicine was achieved with earlier microspore developmental stages than the optimum stages for heat induction and the colchicine was diluted after induction (Zhao et al. 1994). This indicates that heat and colchicine induction are effective on different microspore developmental stages and the removal or dilution of colchicine is important for normal embryo development. The combination treatment of colchicine plus heat followed by washing has been successfully employed to obtain doubled haploids in several *B. napus* cvs. and breeding lines but not in the cv. Topas used herein (Chen et al. 1994, Mollers et al. 1994). It is possible that the combination treatment is effective when a broad range of microspore developmental stages are cultured and when the frequency of embryogenesis is low.

The use of colchicine to induce embryogenesis in microspore cultures and simultaneously double the chromosomes offers a potentially powerful tool for producing pure breeding lines of *B. napus* at high frequencies, a highly desirable combination for plant breeding programs. Furthermore, as all eukaryotic cells are affected similarly by colchicine, i.e through microtubule depolymerization, it is possible that this technique will be applicable to other species, particularly the more recalcitrant ones.

Example 2

Generation of Doubled Haploid Plants with Trifluralin Microspore isolation and culture

*B. napus* cv. Topas, line 4079, was grown as described previously (Telmer et al. 1992). Buds were scored for the stage of microspore development and microspores near the first pollen mitosis were isolated and cultured in NLN-13 culture medium (Telmer et al. 1992). Microspore density was adjusted to 40,000 ml$^{-1}$ NLN-13 medium, and 300 $\mu$l were plated in 10×30 mm Petri dishes (Falcon 1008, VWR Scientific of Canada, Toronto). An additional 300 $\mu$l of NLN-13 medium was added to the control plates and 300 $\mu$l of NLN-13 containing either colchicine or trifluralin at 2× the final concentration was added to the experimental plates. The cultures were incubated in a humid chamber in darkness, for 18 h at 32.5° C. After 18 h at 32.5° C. the cultures were moved to 25° C. where they remained in darkness for 3–4 weeks until cotyledonary embryos developed. When required, the microspores were washed after 18 h of heat treatment to remove colchicine or trifluralin. The contents of each Petri dish was diluted with 1 ml B5 (Gamborg et al. 1968) containing 0.4M mannitol and washed 3× in Eppendorf tubes by centrifugation (100 g, 3 min). After washing, the cells were resuspended in 600 $\mu$l of NLN-13 and cultured at 25° C.

Colchicine and trifluralin stock solutions

Stock solutions of 5 mM colchicine (Sigma, St. Louis, Mo.) and 1 mM trifluralin ($\alpha,\alpha,\alpha$-trifluoro-2,6-dinitro-N-N-dipropyl-p-toluidine) (Eli Lilly and Co., Indianapolis, Ind.) were prepared in double distilled water and in acetone, respectively, and were stored in darkness at 6–9° C. The chemicals were diluted to the required concentration in NLN-13 and filter sterilized prior to use.

Embryo germination and plant regeneration

Cotyledonary embryos were transferred onto solid B5 medium containing 2% sucrose and 0.2% gelrite (Kelco, Merck & Co. Inc., San Diego, Calif.) and cultured at 20° C. and a 16 h photoperiod provided by 115 W Cool White fluorescent lights (Sylvania) and 40 W incandescent lights [Duro Test (90 $\mu$molm$^{-2}$s$^{-1}$)]. The majority of the embryos germinated within 2–3 weeks. Embryos which did not form roots directly were subcultured one or more times on the same medium to induce root development. Plantlets, at the three leaf stage were transferred to soil and vermiculite (1:1) in 1.25 inch pots and grown in a mist chamber for about 2 weeks. They were then repotted in soil in 6 inch pots and grown in the greenhouse at 20/15° C. day/night with a photoperiod of 16 h and supplemented with High Pressure Sodium lucolux lights (General Electric) producing a light intensity of 280 $\mu$molm$^{-2}$s$^{-1}$. Plants with viable pollen were self-pollinated by bagging racemes with unopened buds.

Cytological analysis

Seeds harvested from the selfed plants were germinated on moistened filter paper at 25° C. in darkness and roots were collected 48 h after germination. Roots were placed in ice-water for 3 h followed by a 4 h treatment in 2 mM 8-hydroxyquinoline at 15° C. (Newell et al. 1984) and a 24 h fixation in absolute ethanol:glacial acetic acid (3:1) at room temperature; they were stored in 70% ethanol at 4° C. To stain chromosomes, roots were hydrolysed in 1N HCl at 60° C. for 7 min, stained in Feulgen solution for 1 h followed by 30 min in ice-water and softened with 1% pectinase at room temperature for 5 min. Root meristems were squashed on a slide in 1% aectocarmine and 45% acetic acid and viewed on a Zeiss Axiophot microscope. Technical Pan film (Kodak, Canada) was used for photography.

Microtubule labelling

Microtubules were visualized with indirect immunofluorescence labelling of microspores which were fixed immediately after isolation, and after 0.5, 3, 8, and 18 h of culture. The cells were simultaneously labelled for chromatin with Hoechst 33258 and for microtubules using the primary monoclonal rat anti-yeast tubulin (MAS 078, clone YOL 1/34, Cedarlane Laboratories, Hornby, Ont. Canada) followed by the secondary antibody, fluorescein-conjugated goat anti-rat immunoglobulin IgG (Sigma) (Simmonds et al. 1985; Simmonds and Setterfield 1986). Samples were viewed on a Zeiss Photomicroscope III equipped with epifluorescence optics using filter sets 10(BP450–490+ BP520–560) and 02(G365+LP420) for fluorescein and Hoechst fluorescence, respectively. At least 300 microspores were examined per sample and Ilford XPI-400 film was used for photography.

Depolymerization of microspore microtubules with trifluralin or colchicine

Microspores were cultured in the presence of 0.1, 1.0 and 10 $\mu$M trifluralin and 2.5 and 25 mM colchicine and examined after 0.5, 3, 8 and 18 h of culture. Untreated uninucleate microspores show abundant microtubules radiating from the nuclear envelope. At a concentration of 0.1 $\mu$M, trifluralin did not depolymerize microtubules. However, after 30 min of either 1.0 or 10 $\mu$M trifluralin treatments, all microtubules in uninucleate microspores were depolymerized and at 18 h, microtubule recovery was observed in more than 50% of the microspores in the 1.0 $\mu$M treatment and approx. 30% of the microspores in the 10 $\mu$M treatment. The microtubules did not reorganize into the type of arrays seen prior to the treatment but formed one or several, long, randomly oriented strands (data not shown). Microtubules were not completely depolymerized after 3 h of 25 $\mu$M colchicine treatment but at 8 and 18 h they were no longer visible; 2.5 $\mu$M colchicine did not depolymerize microspore microtubules. At the concentrations tested, neither chemical was effective in depolymerizing microtubules in bicellular microspores; some microtubule depolymerization and disorganization was observed but complete depolymerization was not obtained.

Embryo development

The effect of culturing microspores in the presence of colchicine or trifluralin on embryo frequency and quality is shown in Table 5. The embryo frequencies from microspore cultures treated with the chemicals were lower than the controls. However, the 18 h treatments at the lower concentrations of colchicine and trifluralin produced more embryos than the cultures subjected to continuous treatments and the higher chemical concentrations. Furthermore, the embryos generated from 18 h treatments developed normally whereas abnormal development was prevalent in the continuous treatments with 10 $\mu$M trifluralin, and 25 and 50 $\mu$M colchicine. The embryos classified as abnormal had enlarged cotyledons and swollen hypocotyls or continued enlarging as globular forms but never developed cotyledons.

TABLE 5

Influence of colchicine or trifluralin treatments (18 h or continuous) on the frequency and quality of embryos derived from heat-induced (32.5° C. for 18 h) B. Napus cv. Topas microspores.

| Treatment[a] | No. of experiments | T[b] C | Embryo development |
|---|---|---|---|
| 18 h Treatments | | | |
| Control/washed | 9 | 1.0 | normal |
| 1 $\mu$M trifluralin/washed | 4 | 0.71 ± 0.11 | normal |
| 10 $\mu$M trifluralin/washed | 2 | 0.56 | normal |
| 25 $\mu$M colchicine/washed | 6 | 0.89 ± 0.03 | normal |
| 50 $\mu$M colchicine/washed | 2 | 0.64 | normal |
| Continuous Treatments | | | |
| Control | 9 | 1.0 | normal |
| 1 $\mu$M trifluralin/cont. | 4 | 0.28 ± 0.1 | normal |
| 10 $\mu$M trifluralin/cont. | 2 | 0.06 | abnormal |
| 25 $\mu$M colchicine/cont. | 6 | 0.39 ± 0.01 | abnormal |
| 50 $\mu$M colchicine/cont. | 2 | 0.02 | abnormal |

[a]Microspore cultures were either treated for 18 h and then washed or were cultured continuously (cont.) in the presence of colchicine or trifluralin as described in materials and methods.
[b]Ratio (±SE) of embryo frequency for treated (T) to control (C) embryo frequency for the respective washed or continuous cultures. Actual frequencies of embryogenesis for control/washed and control cultures were 7.4 ± 1.4 and 12 ± 2.0, respectively, and represent the frequency as the percent of total viable microspores.

Influence of colchicine or trifluralin on the generation of fertile plants

More than 85% of the plants regenerated from untreated embryogenic cultures were sterile as they lacked pollen and did not produce seed (Table 6). Cultures treated continuously with 25 $\mu$M colchicine produced fertile plants at a frequency of about 50% (Table 6). However, as the embryos were abnormal (Table 5), even the best of these embryos did not germinate directly and required several subcultures on B5 medium for plantlet development. Plants generated from this treatment were less vigorous and less uniform than those produced from other treatments. When the cultures were washed after 18 h of colchicine treatment, embryo and plant development were normal but only 22% of the regenerated plants were fertile (Tables 5 and 6).

TABLE 6

Fertility of B. napus cv. Topas plants recovered from microspore cultures heat-induced (32.5° C. for 18 h) in the presence of trifluralin or colchicine.

| Treatment | Duration[a] of Treatment | No. fertile plants total plants | % fertile plants |
|---|---|---|---|
| Control | | 6/50 | 12 |
| 25 $\mu$M colchicine | 18 h | 6/27 | 22 |
| 25 $\mu$M colchicine | cont. | 9/17 | 53 |
| 1 $\mu$M trifluralin | 18 h | 14/25 | 56 |

TABLE 6-continued

Fertility of *B. napus* cv. Topas plants recovered from microspore cultures heat-induced (32.5° C. for 18 h) in the presence of trifluralin or colchicine.

| Treatment | Duration[a] of Treatment | No. fertile plants / total plants | % fertile plants |
|---|---|---|---|
| 10 μM trifluralin | 18 h | 7/12 | 58 |
| 1 μM trifluralin | cont. | 15/77 | 20 |
| 10 μM trifluralin | cont. | 0/0 | NA |

[a]Microspore cultures were either treated for 18 h and then washed or were cultured continuously (cont.) in the presence of colchicine or trifluralin as described in materials and methods.

Cultures treated with 1 or 10 μM trifluralin for 18 h generated fertile plants at frequencies approaching 60% (Table 6). The embryos derived from these cultures were normal, germinated readily when transferred to B5 medium and produced vigorous plants. Microspores cultured continuously with 1 μM trifluralin generated fewer fertile plants whereas no plants were regenerated from the 10 μM treatments due to the low embryo frequency and abnormal embryo development (Table 5 and 6).

Cytological analysis of progeny from the fertile plants

Cytological studies were carried out on the progeny of approximately 50% of the fertile plants from each treatment and confirmed the ploidy level to be 2n=38 chromosomes. The chemically induced doubled haploid plants produced seed on all the branches which indicates that they were not chimeric. The fertile plants derived from microspore cultures which had not been treated with colchicine or trifluralin showed the same ploidy level and were not chimeric.

This is the first study to show that trifluralin is an effective chromosome doubling agent and can be used to produce doubled haploid plants of *B. napus*. Fertile plants were obtained from nearly 60% of the plants derived from microspores treated with 1 or 10 μM trifluralin for 18 h. However, 1 μM trifluralin was the better concentration because embryo yield was higher. A great advantage in using trifluralin is that embryogenesis is normal and proceeds to direct embryo germination and vigorous plant growth.

Colchicine treatments of 18 h produced fertile plants at a frequency of only 22%. It is possible that a colchicine treatment of 18 h is too short because it appears to be a slower acting drug than trifluralin as indicated by the 3–8 h required to depolymerize microtubules as compared to 30 min with trifluralin. Other workers have shown that longer treatments with colchicine increased the frequency of chromosome doubling in corn callus (Wan et al. 1989) and the continuous colchicine treatment here produced more than 50% fertile plants. Unfortunately, continuous treatment with colchicine resulted in the production of abnormal embryos requiring time-consuming subcultures and ultimately poor plant development. Similarly, continuous exposure to trifluralin resulted in reduced embryo yields and at a concentration of 10 μM trifluralin resulted in abnormal embryo development. After prolonged exposure to microtubule depolymerizing agents, microtubules recover and plant cells resume normal division and growth; microtubules were beginning to reappear after 18 h of culture in the presence of trifluralin. However, it is unlikely that normal spatial and temporal organization of the cytoskeleton would recover rapidly enough to be synchronized and functional with the next cell cycle. This would impede normal development, as was observed in this and other studies (Hart and Sabnis 1976, Loh and Ingram 1983, Hansen et al. 1988, Mathias and Robbelen 1991). Microtubule recovery is slower at higher concentrations of the depolymerizing agents which would further reduce embryogenic frequency (Table 5).

The generation of fertile non-chimeric plants is most probably a consequence of application of microtubule depolymerizing agents to selected Class III microspore isolations which contained large numbers of late uninucleate microspores (Telmer et al. 1992). Microspores enter mitosis within the first few hours of culture, and by 12 h, the majority had undergone division (Telmer et al. 1994). In the presence of microtubule depolymerizing agents, mitosis proceeds through this stage without a spindle which blocks chromosome segregation but nuclear restitution and the cell cycle proceed normally, except that the chromosome number is doubled (Lignowski and Scott 1972, Zhao and Davidson 1984). The microspores which pass through mitosis early in the culture period would most probably undergo chromosome doubling in the presence of trifluralin which depolymerizes microtubules rapidly. Colchicine, on the other hand requires 3–8 h to depolymerize microtubules and would not affect the early microspore divisions. This may explain why more fertile plants were obtained from cultures treated for 18 h with trifluralin than with colchicine. Furthermore, a high frequency of fertile plants were obtained from the continuous colchicine treatments indicating that the chromosome doubling probably occurred during the second microspore division. It is possible that the microspores subjected to continuous 1, μM trifluralin treatments underwent one cycle of chromosome doubling during the first few hours of culture and a second cycle of doubling prior to recovery of microtubule function. Such polyploid microspores, if they were produced must have ceased further growth because polyploid plants were not recovered. This may explain the reduced embryo frequency and the low frequency of fertile plants obtained from the 1 μM continuous trifluralin treatment.

In conclusion, the addition of a very low concentration of trifluralin to embryogenic microspore cultures of *B. napus* offers a very simple approach to doubling chromosome numbers to generate fertile doubled haploid plants. Microspore embryogenesis is normal and leads to direct germination and development of vigorous plants. It is a time and labor saving alternative to the application of colchicine to plant tissues. Chimeric plants are avoided because chromosomes are doubled very early in culture. The method is simple, effective and inexpensive. Trifluralin has a much higher affinity for plant cells than animal cells and at the concentration used has no effect on animal cells (Bartels and Hilton 1973, Bayer et al. 1967, Hess and Bayer 1977) therefore making it much safer to use than colchicine. As trifluralin has been shown to depolymerize microtubules in diverse plant tissues (Hess and Bayer 1977, Hess 1979, Quader and Filner 1980), it may be equally as effective, as a doubling agent, in other plant species.

All scientific publications and patent documents are incorporated herein by reference.

The present invention has been described with regard to preferred embodiments. However, it will be obvious to persons skilled in the art that a number of variations and modifications can be made without departing form the scope of the invention as described in the following claims.

References

Bamabas, B., P. L. Pfahler, and G. Kovacs, 1991: Direct colchicine on the microspore embryogenesis to produce dihaploid plants in wheat (*Triticum aestivum* L.). Theor. Appl. Genet. 81, 675–678.

Barnabas, B., Pfahler, P. L. & Kovacs, G. 1991. Direct effect of colchicine on the microspore embryogenesis to produce dihaploid plants in wheat (*Triticum aestivum* L).—Theor. Appl. Genet. 81:675–678.

Bartels, P. G. & Hilton, J. L. 1973. Comparison of trifluralin, oryzalin, pronamide, propham and colchicine treatments on microtubules.—Pesticide Biochem. Physiol. 3:462–472.

Bayer, D. E., Foy, C. L., Mallory, T. E. & Cutter, E. G. 1967. Morphological and histological effects of trifluralin on root development.—Am. J. Bot. 54:945–952.

Beversdorf, W. D., Charne D. G., Kott, L. S., Chuong, P. V., Polsoni, L. & Zilka, J. 1987. The utilization of microspore culture and microspore-derived doubled-haploids in a rapeseed (*Brassica napus*) breeding program.—In Proc. 7th Int. Rapeseed Conf, (Organizing Committee, ed), pp. 13. Poznan, Poland.

Burk, L. G., G. R. Gwynn, G. F. Chapline, 1972: Diploidized haploids from aseptically cultured anthers of *Nicotiana tabacum*: A colchicine method applicable to plant breeding. J. Hered. 63, 355–360.

Carpenter, J. L., Ploense, S. E., Snustad, D. P., Silflow, C. D. (1992) Preferential expression of an α-tubulin gene of Arabidopsis in pollen. Plant Cell 4, 557–571.

Charne, D. G., P. Pukacki, L. S. Kott, W. D. Beversdorf, 1988: Embryogenesis following cryopreservation in isolated microspores of rapeseed (*Brassica napus* L.). Plant Cell Rep. 7, 407–409.

Gamborg, O. L., Miller, R. A., Ojima, J. (1968) Nutrient requirements of suspension cultures of soybean root cells. Exp. Cell Res. 50, 151–158.

Gland, A., Lichter, R., Schweiger, H. G. (1988) Genetic and exogenous factors affecting embryogenesis in isolated microspore cultures of *Brassica napus* L. J. Plant Physiol. 132, 613–617.

Gunning, B. E. S., Hardham, A. R. (1982) Microtubules. Annu. Rev. Plant Physiol. 33, 651–698.

Hansen, F. L., I. K. D. Andersen, and A. Olesen, 1988: Nitrous oxide as a possible alternative agent for chromosome doubling of wheat haploids. Plant Sci. 54, 219–222.

Hart, J. W. & Sabnis, D. D. 1976. Colchicine and plant microtubules: A critical evaluation.—In Commentaries in Plant Sci. (H. Smith, ed), pp. 1095–1104. Pergamon Press, Oxford, N.Y. ISBN 0-080-19759-0.

Hassawi, D. S. & Liang, G. H. (1991) Antimitotic agents: Effects on doubled haploid production in wheat. Crop Sci. 31:723–726.

Hess, F. D. & Bayer, D. E. 1977. Binding of the herbicide trifluralin to Chlamydomonas flagellar tubulin.—J. Cell Sci. 24:351–360.

Hess, F. D. 1979. The influence of herbicide trifluralin on flagellar regeneration in Chlamydomonas.—Exp. Cell Res. 119:99–109.

Huang, B., Bird, S., Kemble, R., Simmonds, D., Keller, W., Miki, B. (1990) Effects of culture density, conditioned medium and feeder cultures on microspore embryogenesis in *Brassica napus* L. cv. Topas. Plant Cell Rep. 8, 594–597.

Chen, J. L., Beversdorf, W. D. (1992) Production of spontaneous diploid lines from isolated microspores following cryopreservation in spring Rapeseed (*Brassica napus* L.). Plant Breeding 108, 324–327.

Chen, Z. Z., Snyder, Z., Fan, Z. G., Loh, W. H. (1994) Efficient production of doubled haploid plants through chromosome doubling of isolated microspores in *Brassica napus*. Plant Breeding 113, 217–221.

Chuong, P. V., Beversdorf, W. D. (1985) High frequency embryogenesis through isolated microspore culture in *Brassica napus* L and *B. carinata* Braun. Plant Sci. 39, 219–226.

Cleveland, D. W., Pittenger, M. F., Feramisco, J. R. (1983) Elevation of tubulin levels by microinjection suppresses new tubulin synthesis. Nature 305, 738–740.

Collins, G. B. & Genovesi, A. D. 1982. Anther culture and its application to crop improvement. In Application of plant cell and tissue culture to agriculture and industry. (D. T. Tomas, B. E. Ellis, K. J. Kasha and R. L. Peterson, eds), pp. 1–24. Univ Guelph.

Cordewener, J. H. G., Businck, R., Traas, J. A., Custers, J. B. M., Dons, H. J. M., Van Lookeren Campagne, M. M. (1994) Induction of microspore embryogenesis in *Brassica napus* L. is accompanied by specific changes in protein synthesis. Planta 19 195, 50–56.

Depaepe, R., Bleton, D. & Gnangbe, F. 1981. Basis and extent of genetic variability among doubled haploid plants obtained by pollen culture in *Nicotiana sylvestris*.—Theor. Appl. Genet. 59: 177–184.

Fan, Z., Armstrong, K. C., Keller, W. A. (1988) Development of microspores in vivo and in vitro in *Brassica napus* L. Protoplasma 147, 191–199.

Huang, B. (1992) Genetic manipulation of microspores and microspore-derived embryos. In Vitro Cell Dev. Biol. 28, 53–58.

Iqbal, M. C. M., Mollers, C., Robbelen, G. (1994) Increased embryogenesis after colchicine treatment of microspore cultures of *Brassica napus* L. J. Plant Physiol. 143, 222–226.

Kasperbauer, M. J. & Collins, G. B. 1972. Reconstitution of diploids from leaf tissue of anther-derived haploids in tobacco.—Crop Sci. 12:98–101.

Keller, W. A., Arnisn, P. G., Cardy, B. J. (1986) Haploids from gametophytic cells—recent developments and future prospects. In: Plant Tissue and Cell Culture. Proc. 6th Int. Tissue Culture Congr. pp. 223–241, Green, C. E., Somers, D. A., Hacoett, W. P., Biesboer, D. D., eds. Alan R Liss Inc., New York, N.Y. ISBN 0-8-45118-021.

Keller. W. A., Armstrong, K. C. (1978) High frequency production of microspore-derived plants from *Brassica napus* anther culture. Z. Pflanzenzuchtg. 80, 100–108.

Keller, W. A. and K. C. Armstrong, 1977: Embryogenesis and plant regeneration in *Brassica napus* anther cultures. Can. J. Bot. 55, 1383–1388.

Kott, L. S., Polsoni, L., Beversdorf, W. D. (1988) Cytological aspects of isolated microspore culture of *B. napus*. Can. J. Bot. 66, 1658–1664.

Ku, M. K., Chen, W. C., Kuo, L. C., Kuan, Y. L., An, H. P. & Huang, C. H. 1981. Induction factors and morphocytological characteristics of pollen-derived plants in maize (*Zea mays*).—In Proc. Symposium Plant Tissue Culture. pp. 35–41. Pitman Publishing Ltd. and The Sci. Press, Peking, ISBN 0-237-08488-7.

Lau, J. T. Y., Pittenger, M. F., Cleveland, D. W. (1985) Reconstruction of appropriate tubulin and actin gene regulation and-actin genes. Mol. Cellular Biol. 5, 1611–1620.

Levan, A. 1938. Effects of colchicine on root mitosis in Allium.—Hereditas 24:471–486.

Lichter, R. (1981) Anther culture of *Brassica napus* in a liquid medium. Z. pflanzenphysiol. 103, 229–237.

Lichter, R. 1982. Induction of haploid plants from isolated pollen of *Brassica napus*.—Z. Pflanzenphysiol. 105:427–434.

Lignowski, E. M. & Scott, E. G. 1972. Effect of trifluralin on mitosis.—Weed Sci. 20:267–270.

Loh, C.-S. and D. S. Ingram, 1983: The response of haploid secondary embryoids and secondary embryogeneic tissues of winter oilseed rape to treatment with colchicine. New Phytol. 95, 359–366.

Margolis, R. L., Wilson, L. (1977) Addition of colchicine-tubulin complex to microtubule ends: the mechanism of substoichiometric colchicine poisoning. Proc. Natl. Acad. Sci. 74, 3466–3470.

Mathias, R., and G. Robbelen, 1991: Effective diploidization of microspore-derived haploids of rape (*Brassica napus*) by in vitro colchicine treatment. Plant Breeding 106, 82–84.

Mineyuki, Y., Gunning, B. E. S. (1990) A role for prepro- phase bands of microtubules in maturation of new cell walls, and a general proposal on the function of 4 pre- prophase band sites in cell division in higher plants. J. Cell Sci. 97, 527–537.

Morejohn, L. C. & Fosket, D. E. 1984. Taxol-induced rose microtubule polymerization in vitro and its inhibition by colchicine.—J. Cell Biol. 99:141–147.

Morejohn, L. C., Bureau, T. E., Tocchi, L. P. & Fosket, D. E. 1984. Tubulins from different higher plant species are immunologically nonidentical and bind colchicine differentially.—Proc. Natl. Acad. Sci. 81:1440–1444.

Newell, C. A., Rhoads, M. L. & Bidney, D. L. 1984. Cytogenetic analysis of plants regenerated from tissue explants and mesophyll protoplasts of winter rape, *B. napus* L.—Can. J. Genet. Cytol. 26:752–761.

Pechan, P. M., Bartels, D., Brown, D. C. W., Schell, J. (1991) Messenger-RNA and protein changes associated with induction of *Brassica napus* embryogenesis. Planta 184, 17, 161–165.

Pechan, P. M., Keller. W. A. (1989) Induction of microspore embryogenesis in *Brassica napus* L. by gamma irradia- tion and ethanol stress. In Vitro Cell Dev. Biol. 25, 1073–1075.

Probst, G. W., Golab, T. & Wright, L. 1976. Dinitroanilines.—In Herbicides. (P. C. Kearney and D. D. Kaufman, eds), pp. 453–500. Marcell Dekker Inc., New York.

Quader, H. & Filner, P. 1980. The action of antimytotic herbicides on flagellar regeneration in *Chlamydomonas reinhardii*: a comparison with the action of colchicine.— European. J. Cell Biol. 21:301–304.

Simmonds, D. H. (1986) Prophase bands of microtubules occur in protoplast cultures of Vicia hajastana Grossh. Planta 167, 469–472.

Simmonds, D. H. (1994) Mechanism of induction of microspore embryogenesis in *Brassica napus*: signifi- cance of the preprophase band of microtubules in the first sporophytic division. In: Biomechanics of active move- ment and division of cells. NATO ASI series, Vol. H 84, Akkas, N., ed. pp. 569–574, Springer-Verlag, Berlin.

Simmonds, D. H., Gervais, C., Keller, W. A. (1991) Embryo- genesis from microspores of embryogenic and non- embryogenic lines of *Brassica napus*. In: Proceedings GCIRC 8th International Rapeseed Congress, pp. 306–311, McGregor D. I., ed. Saskatoon, Sask, Canada.

Simmonds, D. H. & Setterfield, G. 1986. Aberrant micro- tubule organization can result in genetic abnormalities in protoplast cultures of *Vicia hajastana* Grossh.—Planta 167:460–468.

Simmonds, D. H., Seagull, R. W. & Setterfield, G. 1985. Evaluation of techniques for immunofluorescent staining of microtubules in cultured plant cells.—J. Hist. and Cytochem. 33:345–352.

Srivastava, P. S., Johri, B. M. (1988) Pollen embryogenesis. J. Palynology. 23, 83–99.

Sternlicht, H., Ringel, I., Szasz, J. (1983) Theory for mod- elling the copolymerization of tubulin and tubulin-colchicine complex. Biophys. J. 42, 255–267.

Subrahmanyam, N. C. and K. J. Kasha, 1975: Chromosome doubling of barley haploids by nitrous oxide and colchi- cine treatment. Can. J. Genet. Cytol. 17, 573–583.

Sunderland, N., Collins, G. B. & Dunwell, J. M. 1974. The role of nuclear fusion in pollen embryogenesis of *Datura innoxia* Mill.—Planta 117:227–241.

Swanson, E. B., Herrgesell, M. J., Arnoldo, M., Sippell, D. W. Wong, R. S. C. (1989) Microspore mutagenesis and selection: Canola plants with field tolerance to the imi- dazolinones. Theor. Appl. Genet. 78, 525–530.

Swanson, E. R. 1990. Microspore culture in Brassica.—In Methods in Molecular Biol. Vol. 6: Plant Cell and Tissue Culture Techniques. (J. W. Pollard and J. M. Walker eds), pp. 159 169. Humana Press, ISBN 0-685-38212-5.

Telmer, C. A., Newcomb, W., Simmonds, D. H. (1994) Cellular changes during heat shock induction and embryo development of cultured microspores of *Brassica napus* cv. Topas. Protoplasma. In Press.

Telmer, C. A., Newcomb, W., Simmonds, D. H. (1993) Microspore development in *Brassica napus* and the effect of high temperature on division in vivo and in vitro. Protoplasma. 172, 154–165.

Telmer, C. A., Simmonds, D. H., Newcomb, W. (1992) Determination of developmental stage to obtain high frequencies of embryogenic microspores in *Brassica napus*. Physiologia Plantarum 84, 417–424.

Terasaka, O., Niitsu, T. (1990) Unequal cell division and chromatin differentiation in pollen grain cells II. Micro- tubule dynamics associated with the unequal cell division. Bot. Mag. Tokyo 103, 133–142.

Van Lammeren, A. A. M., Keijzer, C. J., Willemse, M. T. M., Kieft, H. (1985) Structure and function of the microtu- bular cytoskeleton during pollen development in Gasteria verrucosa (Mill.) H. Duval. Planta 165, 1–11.

Vierling, E. (1991) The roles of heat shock proteins in plants. Annu. Rev. Plant Physiol Plant Mol. Biol. 42, 579–620.

Wan, Y., J. F. Petolino, and J. M. Widholm, 1989: Efficient production of doubled haploid plants through colchicine treatment of anther-derived maize callus. Theor. Appl. Genet. 77, 889–892.

Wenzel, G., F. Hoffmann, and E. Thomas, 1976: Heterozy- gous microspore-derived plants in rye. Theor. Appl. Genet. 48, 205–208.

Wenzel, G., Hoffmann, F. & Thomas, E. 1977. Anther culture as a breeding tool in rape: I. ploidy level and phenotype of androgenic plants.—Z. Pflanzenzuchtg. 78:149–155.

Wong, C. K. 1989. A new approach to chromosome doubling for haploid rice plants.—Theor. Appl. Genet. 77: 149–151.

Zaki, M. A. M., Dickinson, H. G. (1991) Microspore- derived embryos in Brassica: the significance of division symmetry in pollen mitosis I to embryogenic develop- ment. Sex. Plant Reprod. 4, 48–555.

Zhao, J.-P. and D. Davidson, 1984: Distribution of chromo- somes into discrete group in colchicine-induced C-metaphases of barley. Caryologia 37, 331–342.

The embodiment of the invention in which an exclusive property or privilege is claimed are defined as follows:

1. A method of inducing embryogenesis from plant microspores comprising:
   treating a microspore plant culture with colchicine at about 25° C.; and incubating for a sufficient time to induce embryogenesis.

2. The method of claim 1 wherein the method further induces chromosome doubling.

3. The method of claim 2 wherein the colchicine is from about 12.5 $\mu$M to about 100 $\mu$M.

4. The method of claim 3 wherein the colchicine is from about 25 μM to about 50 μM.

5. The method of claim 4 wherein the sufficient time is from about 15 to about 50 hours.

6. The method of claim 5 wherein the sufficient time is from about 18 to about 42 hours.

7. The method of claim 6 wherein the method further comprises reducing the concentration of colchicine in the microspore culture and incubating at about 25° C. until an embryo is formed.

8. The method of claim 7 wherein the microspore plant culture is a *Brassica napus* culture.

9. The method of claim 1 wherein the treating step is by culturing in the presence of a medium containing the colchicine.

10. The method of claim 1 wherein the treating step is by a biolistic delivery system.

11. A method of inducing embryogenesis and chromosome doubling from plant microspores comprising;

treating a microspore plant culture of *B. napus* with about 25 μM to about 50 μM of colchicine at about 25° C.; incubating the microspore plant culture for about 18 to about 42 hours to induce embryogenesis and chromosome doubling; reducing the colchicine to about 12.5 μM by dilution; and incubating at about 25° C. for 3 to 4 weeks until an embryo is formed.

* * * * *

UNITED STATES PATENT AND TRADEMARK OFFICE
CERTIFICATE OF CORRECTION

PATENT NO. : 5,900,375
DATED : May 4, 1999
INVENTOR(S) : Simmonds et al.

It is certified that error appears in the above-identified patent and that said Letters Patent is hereby corrected as shown below:

<u>Title page,</u>
Item [75], Inventors: please delete "Newcombe" and replace with -- Newcomb --.

Item [73], Assignees:
Please delete "Her Majesty the Queen in right of Canada, as represented by Agriculture: Agri-Food Canada, a part interest, both of Ottawa, Canada" and replace with -- Her Majesty In Right Of Canada As Represented By The Minister Of Agriculture And Agri-Food Canada, of Ottawa, Ontario, Canada, --

After Item" [22], Filed: Mar. 29, 1996", insert the following:
-- Item: [30], Foreign Application Priority Data: March 29, 1995 [CA] Canada ....... 2,145,833 --.

Signed and Sealed this

Sixteenth Day of April, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 5,900,375
DATED : May 4, 1999
INVENTOR(S) : Simmonds et al.

It is certified that error appears in the above-identified patent and that said Letters Patent is hereby corrected as shown below:

Title page,
Item [75], Inventors, please delete "Newcombe" and replace with -- Newcomb --.
Item [73], Assignees, please delete "Her Majesty the Queen in right of Canada, as represented by Agriculture; Agri-Food Canada, a part interest, both of Ottawa, Canada" and replace with -- Her Majesty In Right Of Canada As Represented By The Minister Of Agriculture And Agri-Food Canada, of Ottawa, Ontario, Canada, a part interest --
After Item [22], insert the following item:

-- [30]   Foreign Application Priority Data
March 29, 1995 [CA]  Canada ..........2,145,833 --.

Signed and Sealed this

Twelfth Day of October, 2004

JON W. DUDAS
*Director of the United States Patent and Trademark Office*